US011077623B2

(12) United States Patent
Bühler et al.

(10) Patent No.: US 11,077,623 B2
(45) Date of Patent: Aug. 3, 2021

(54) DEVICE FOR WELDING TUBES

(71) Applicant: Reed Electronics AG, Schachen (CH)

(72) Inventors: Peter Bühler, Schwarzenberg (CH); Willy Fluder, Malters (CH); Markus Wyss, Schwarzenberg (CH)

(73) Assignee: REED ELECTRONICS AG, Schachen (CH)

( * ) Notice: Subject to any disclaimer, the term of this patent is extended or adjusted under 35 U.S.C. 154(b) by 15 days.

(21) Appl. No.: 15/780,091

(22) PCT Filed: Nov. 29, 2016

(86) PCT No.: PCT/EP2016/079073
§ 371 (c)(1),
(2) Date: May 30, 2018

(87) PCT Pub. No.: WO2017/093216
PCT Pub. Date: Jun. 8, 2017

(65) Prior Publication Data
US 2018/0345589 A1 Dec. 6, 2018

(30) Foreign Application Priority Data
Nov. 30, 2015 (CH) ...................... 1751/15

(51) Int. Cl.
*B29C 65/00* (2006.01)
*B29C 65/20* (2006.01)
(Continued)

(52) U.S. Cl.
CPC ....... *B29C 65/2046* (2013.01); *A61M 39/146* (2013.01); *B29C 65/2076* (2013.01);
(Continued)

(58) Field of Classification Search
CPC .............. B29C 65/2046; B29C 66/857; B29C 66/8432; B29C 66/1142; B29C 66/73921; Y10T 156/1317; Y10T 156/1322
See application file for complete search history.

(56) References Cited

U.S. PATENT DOCUMENTS

| 4,610,670 A | 9/1986 | Spencer |
| 7,779,880 B2 * | 8/2010 | Sano ...................... B29C 66/96 |
| | | 156/353 |
| 2012/0269679 A1 | 10/2012 | Payrat et al. |

FOREIGN PATENT DOCUMENTS

| CH | 698798 B1 | 10/2009 |
| EP | 0208004 A1 | 1/1987 |

(Continued)

OTHER PUBLICATIONS

International Search Report from the European Patent Office dated Feb. 8, 2017 for corresponding International Application No. PCT/EP2016/079073.

(Continued)

*Primary Examiner* — Mark A Osele
*Assistant Examiner* — Christopher C Caillouet
(74) *Attorney, Agent, or Firm* — Walter Haverfield LLP; Sean F. Mellino

(57) ABSTRACT

A device for welding thermoplastic tubes to a welding method, and to a welding knife. The device is provided for welding thermoplastic tubes, wherein the tubes are placed into tube holders and squeezed with the aid of tube clamps. A welding knife is moved between the first and the second tube holder and severs the tubes in the process. Cut ends and residual ends are thereby produced. The cut ends are aligned with one another by a relative movement of one tube holder with respect to the other tube holder and, by a horizontal (Continued)

movement of the two tube holders, are welded simultaneously to form continuous tubes.

15 Claims, 14 Drawing Sheets

(51) Int. Cl.
   *B29C 65/30* (2006.01)
   *B29C 65/78* (2006.01)
   *A61M 39/14* (2006.01)
(52) U.S. Cl.
   CPC .......... *B29C 65/30* (2013.01); *B29C 65/7802* (2013.01); *B29C 65/7841* (2013.01); *B29C 66/1142* (2013.01); *B29C 66/5221* (2013.01); *B29C 66/73921* (2013.01); *B29C 66/8161* (2013.01); *B29C 66/8167* (2013.01); *B29C 66/8432* (2013.01); *B29C 66/857* (2013.01); *B29C 66/919* (2013.01); *B29C 66/91216* (2013.01); *B29C 66/91231* (2013.01); *Y10T 156/1317* (2015.01); *Y10T 156/1322* (2015.01)

(56) References Cited

FOREIGN PATENT DOCUMENTS

| | | |
|---|---|---|
| EP | 0643975 A1 | 3/1995 |
| RU | 108334 U1 | 9/2011 |
| WO | 2008/005882 A2 | 1/2008 |

OTHER PUBLICATIONS

Written Opinion from the European Patent Office dated Feb. 8, 2017 for corresponding International Application No. PCT/EP2016/079073.

\* cited by examiner

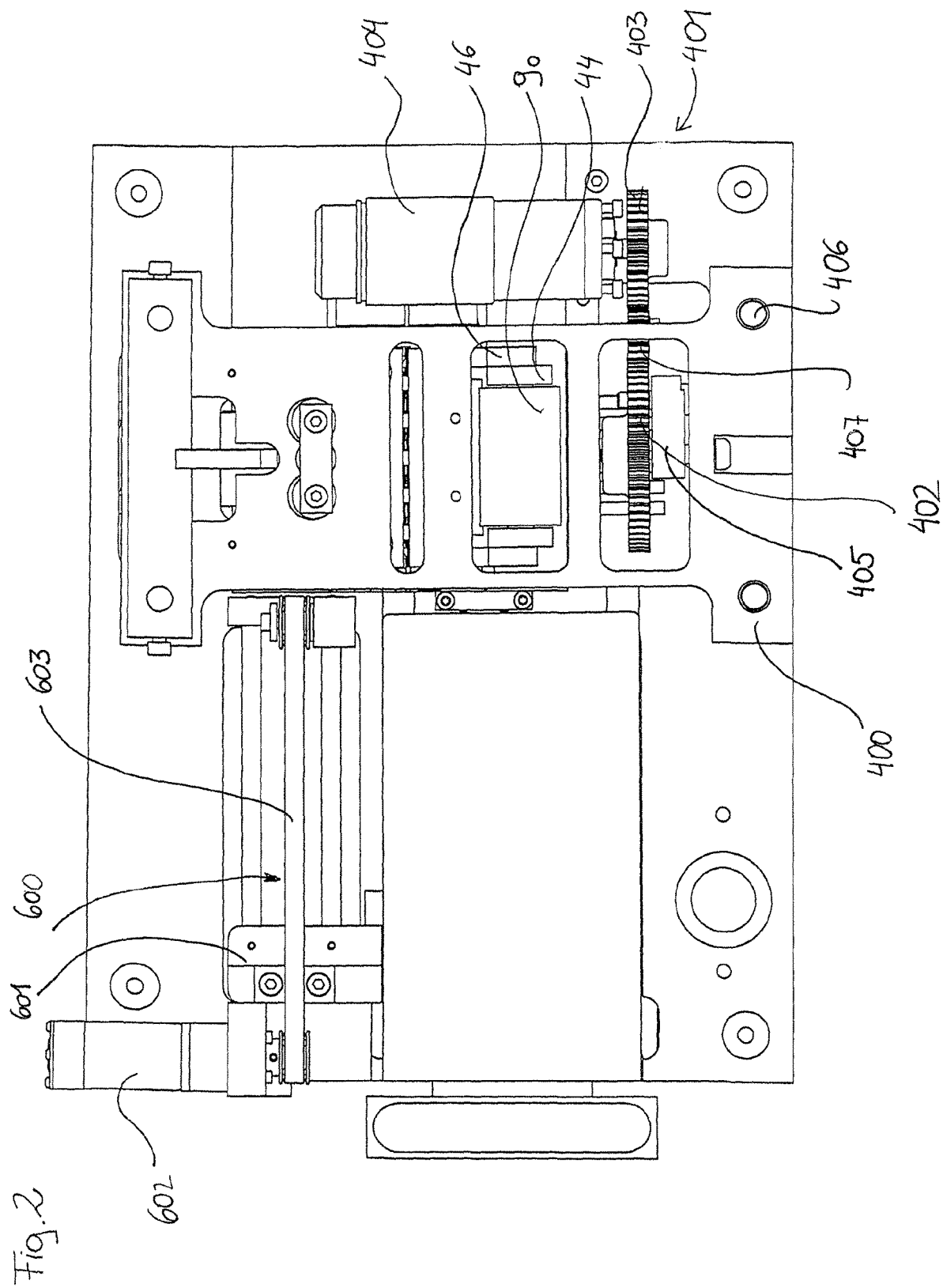

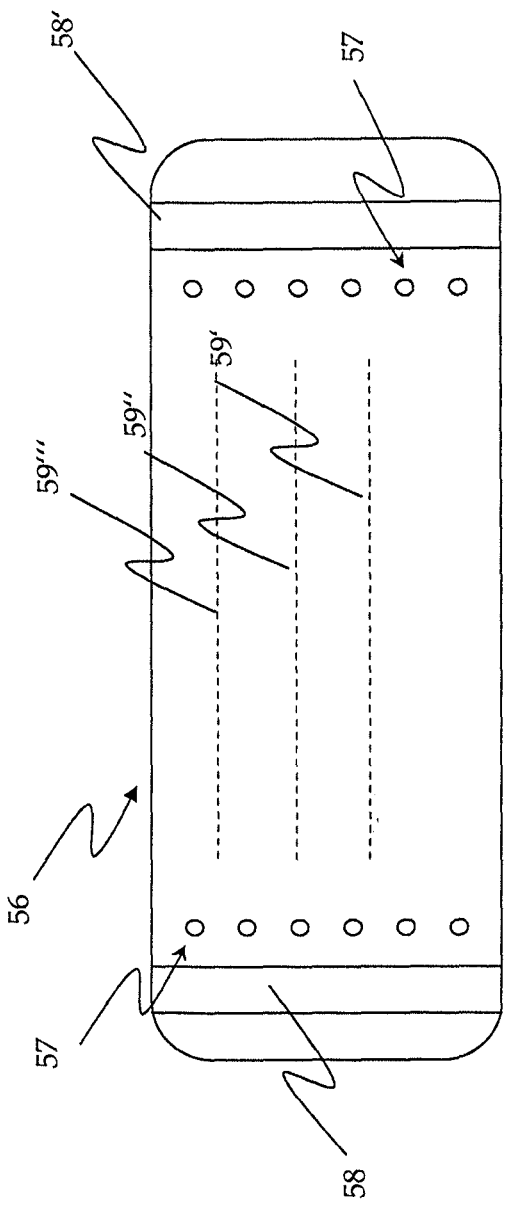
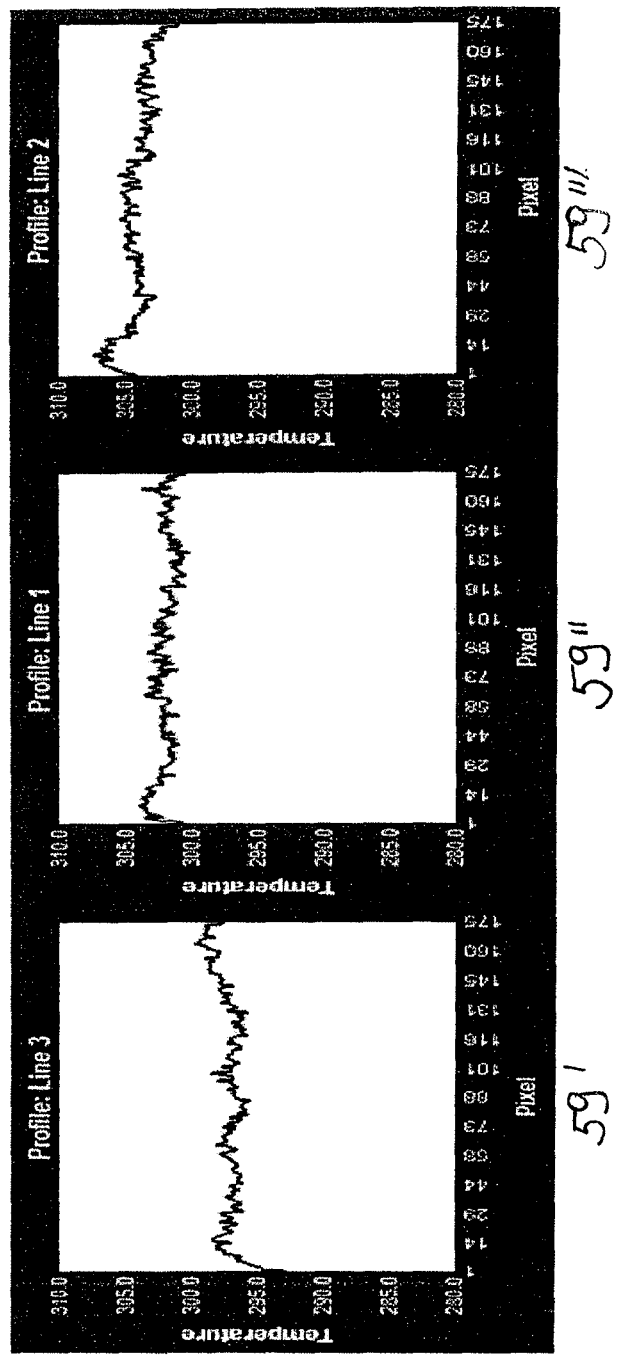
Fig. 11

DEVICE FOR WELDING TUBES

CROSS-REFERENCE TO RELATED APPLICATIONS

This application is a National Stage application of International Application No. PCT/EP2016/079073 filed on Nov. 29, 2016, which claims priority of Swiss (CH) application Serial Number 1751/15 filed on Nov. 30, 2015, both of which are incorporated herein by reference in their entireties.

BACKGROUND OF THE INVENTION

Field of the Invention

The invention pertains to a device for welding tubes, to a welding method and to a welding knife.

Description of the Prior Art

U.S. Pat. No. 4,610,670 A discloses a device and a method for producing a sterile connection between two thermoplastic tubes. In this method, a connection is produced between the ends of two tubes, one end of which respectively leads into a blood bag. For this purpose, the two tubes are inserted into two spaced-apart blocks parallel to one another, severed with a heated knife and joined into a continuous tube. The aim is to produce a sterile connection between two tubes.

EP0208004 A1 discloses a method and a device for docking tubular plastic sections in a sterile manner. Comparably to U.S. Pat. No. 4,610,670 A, two tube ends are also joined into a continuous tube in this case, but two already cut tube ends are clamped into holding blocks and heated by a heating device, as well as joined and welded to one another by means of a horizontal displacement of the holding blocks relative to one another.

US 2012/0269679 A1 discloses a system, by means of which a plurality of tubes, one end of which is respectively connected to a blood bag, can be welded to a plurality of tubes leading into a so-called "pooling container." In the disclosed method, individual heated blades are used for severing the tubes and for welding together the tubes in an additional step.

SUMMARY OF THE PRESENT INVENTION

Highly automated process sequences are used in the processing of donor blood units. Consequently, a machine used for this purpose has to meet strict requirements with respect to efficiency and sterility. One essential step comprises interconnecting multiple blood bags by welding the tubes leading away from the individual bags to one another. In blood banks, more than 2000 welding operations per day are carried out on hundreds of blood bags in order to connect the individual donor blood units, e.g., for producing platelet concentrate from donor blood. It is therefore necessary to carry out as many welding operations as possible within the shortest period of time possible and with consistently high quality. A sterile connection should be produced in this case. The invention is based on the objective of making available a device and a method for welding a plurality of thermoplastic tubes, which provide the above-described advantages and eliminate the disadvantages of the prior art.

The invention furthermore aims to make available a device, a method and a heatable welding knife for cutting a plurality of thermoplastic tubes and welding together their ends with consistent quality. These objectives are attained with the characteristics of the claims.

Preferred embodiments of the invention are disclosed in the dependent claims.

The inventive device for welding thermoplastic tubes of a first and a second group of tubes comprises two tube holders that respectively comprise a first and a second tube clamp, as well as a welding knife. The tubes of the first group of tubes continuously extend between the two tube holders in a straight manner, are inserted into the through-openings of the two first tube clamps and squeezed therein.

The tubes of the second group of tubes also continuously extend between the two tube holders in a straight manner, are inserted into the through-openings of the two second tube clamps and squeezed therein.

The welding knife is moved between the first and the second tube holder and is provided for severing the squeezed tubes of the first and the second group of tubes in one motion in order to thereby produce cut ends and residual ends.

One of the two tube holders can be displaced relative to the other tube holder in order to thereby align the cut ends of the tubes with one another.

The two tube holders can furthermore be displaced toward one another or away from one another in a horizontal direction in order to thereby simultaneously weld each cut end of a tube of the first group of tubes and each cut end of a tube of the second group of tubes into respective continuous tubes.

An advantage of the inventive device can be seen in that a plurality of thermoplastic tubes can thereby be welded into continuous tubes in a sterile manner with a reduced number of work steps.

According to the invention, the through-openings of the two first tube clamps are arranged on a first plane and the through-openings of the two second tube clamps are arranged on a second plane, wherein the first plane is arranged parallel to the second plane and spaced apart therefrom.

In a preferred embodiment of the invention, the two first tube clamps and the two second tube clamps comprise squeezing zones, wherein these squeezing zones extend along the through-openings and are provided for squeezing the inserted tubes at an oblique angle in relation to the first and/or the second plane respectively.

According to the invention, the welding knife can be clamped in a welding knife holder and a drive unit is provided for moving the welding knife holder in a vertical direction in order to sever the tubes. During the motion in the vertical direction, one of the two tube holders is vertically displaced relative to the other tube holder in order to align the cut ends of the tubes. According to the invention, the two tube holders are furthermore horizontally moved toward one another or away from one another or both tube holders are simultaneously moved in one direction due to the motion of the welding knife holder in the vertical direction.

In a preferred embodiment, the device comprises a platform that can be moved in the vertical direction and the welding knife holder is arranged on this platform.

According to the invention, the welding knife holder comprises two opposite clamping parts, between which the welding knife can be clamped. It is preferred that one of the two clamping parts is stationary and the other clamping part can be moved relative to the stationary clamping part.

A pair of first crank brackets is furthermore provided on one of the two clamping parts. In an embodiment, the clamping part and the pair of first crank brackets are realized in one piece. Alternatively, the pair of first crank brackets is mounted on one of the two clamping parts in the form of separate components.

The pair of crank brackets preferably comprises a total of four first cranks. These cranks are identical to one another and arranged mirror-symmetrical referred to a plane of the welding knife when the welding knife is clamped between the two clamping parts.

Furthermore, pairs of tracer wheels are provided in order to trace the cranks during the motion of the welding knife holder in the vertical direction and to thereby move the tube holders horizontally toward one another or away from one another or to simultaneously move both tube holders in one direction.

According to the invention, a second crank bracket and an additional tracer wheel are provided. The additional tracer wheel is provided for tracing the second crank bracket during the motion of the welding knife holder in the vertical direction. In the process, one clamping part is moved relative to the second stationary clamping part and the distance between the two clamping parts is thereby varied.

The distance between the two clamping parts is preferably varied in three different positions while the second crank bracket is traced by the second tracer wheel.

In a pickup position, the tracer wheel is in contact with the second crank bracket and the resulting distance between the two clamping parts just suffices for the insertion of the welding knife.

In a contacting position, the distance between the two clamping parts is chosen such that the welding knife is clamped in position and at the same time electrically contacted. In this position, the tracer wheel is not in contact with the second crank bracket.

In a release position, the tracer wheel is in contact with the second crank bracket and the distance between the two clamping parts is chosen such that the welding knife can be ejected.

In a preferred embodiment, pressure pads are arranged on at least one of the two clamping parts and contact the welding knife in the contacting position. In an embodiment, these pressure pads are spring-mounted on at least one clamping part. Due to this spring mounting, the pressure exerted upon the welding knife when it is contacted can be variably adjusted. It was determined that a largely regular pressure distribution upon the welding knife results in a regular pressure distribution over the surface of the welding knife. A largely uniform distribution is desirable because this improves the quality of the weld. In this case, it is ensured that comparable thermal energy is respectively applied to the cut ends and the residual ends of the thermoplastic tubes regardless of their position in the tube holder.

According to the invention, the device comprises a transformer unit with a primary winding and a secondary winding, wherein the secondary winding is formed by a single conductor only. This conductor is connected to one of the two clamping parts, preferably to the stationary clamping part. In the contacting position, the welding knife closes the secondary circuit and forms the primary resistance element, in which the power loss predominantly occurs, in this secondary circuit. In this way, the welding knife is heated to the desired temperature. The welding knife is particularly heated to a temperature of around 300° C. with a high alternating current. The inventive arrangement made it possible to achieve a constant heating power on the welding knife. Due to the inventive design, the electrical system can be easily integrated into the housing of the device. According to the invention, the first and the second group of tubes respectively comprise the same number of individual tubes, preferably more than two tubes, particularly six tubes per group of tubes.

The inventive method for welding a plurality of tubes of a first and a second group of tubes by means of the inventive device comprises multiple steps.

The tubes of the first and the second group of tubes are initially inserted parallel to and on top of one another into opposite first and second tube holders, namely such that they continuously extend between said tube holders in a straight manner, and squeezed therein. A heatable welding knife is inserted into a welding knife holder and heated to a desired temperature.

The heated welding knife is moved between the first and the second tube holder such that the squeezed tubes are simultaneously severed into cut ends and residual ends.

The cut ends of the tubes are molten by the heated welding knife.

The cut ends of the tubes of the first group of tubes are aligned with the cut ends of the tubes of the second group of tubes by displacing one of the two tube holders relative to the other tube holder such that the cut ends of the tubes of the first group of tubes are arranged symmetrically opposite of the cut ends of the second group of tubes and the welding knife can be retracted.

The two tube holders are displaced toward one another in order to thereby simultaneously weld each cut end of the tubes of the first group of tubes and each cut end of the tubes of the second group of tubes into respective continuous tubes.

The welding knife is ultimately ejected from the welding knife holder.

During the insertion of the welding knife (4), the horizontal distance between the first and the second tube holder (100, 200) amounts to d1. This distance is increased to d4 when the squeezed tubes are severed. When the cut ends are molten, the distance amounts to d2, wherein d1<d2<d4 applies. The distance is once again increased to d4 during the displacement of one of the two tube holders (100, 200). The distance amounts to d3 during the welding operation, wherein d3<d4 applies, and the distance between the two tube holders (100, 200) amounts to d5 during the ejection of the welding knife, wherein d5 represents the shortest of all five distances.

The size of the distance d4 is chosen in such a way that a tensile stress is applied to the thermoplastic tubes. Severing of the tubes is thereby simplified. The distance is reduced to d2 when the cut ends are molten. In this way, the cut ends and the residual ends contact the heated welding knife and are correspondingly molten on their cross sections. The distance is once again increased to d4 during the displacement of one of the two tube holders. The increase of the distance to d4 ensures that sufficient molten material for the subsequent welding operation remains on the tube cross sections when the welding knife is retracted. Subsequently, each cut end of a tube of the first group of tubes and each cut end of a tube of the second group of tubes are simultaneously welded into respective continuous tubes in that the ends are joined by reducing the distance between the tube holders to d3. Ultimately, the welding knife is ejected and the welded tubes are removed. The tube holders are spaced apart by the distance d5, which is typically so small that they contact one another.

The inventive welding knife, which is preferably used in the inventive device and in the inventive method, comprises a plurality of recesses in its cutting surface. According to the invention, the cutting surface serves for respectively melting the cut ends and the residual ends, which is the reason why it is referred to as melting surface below.

It was determined that the recesses and, in particular, their arrangement and/or number affect the vertical and the horizontal temperature distribution over the welding knife surface. A regular distribution is advantageous because largely uniform melting of the cut ends of the thermoplastic tubes, as well as a sound welding result, is thereby ensured.

In a preferred embodiment, the melting surface has a rectangular shape and peripheral zones are provided along the two short sides of the rectangle, wherein said peripheral zones are provided for contacting a secondary side of a transformer unit. This contacting is preferably realized by means of the pressure pads arranged on one of the two clamping parts.

The recesses in the melting surface are arranged along the peripheral zones of the melting surface.

The inventive welding knife comprises a blade on one of the two longer sides of the rectangle, wherein the blade has a symmetric shape referred to the cross section of the rectangle. This shape is advantageous because the welding knife thereby produces a very straight cut when it severs the tubes.

In an embodiment, the welding knife is produced by longitudinally folding a lamella of double width in half. In this case, the bending edge, along which the two halves of the lamella are connected to one another, serves as the blade for cutting the tubes. In this way, a symmetrically rounded blade is produced.

As an alternative to this folded design, the welding knife may be produced by means of punching and its blade may be produced by means of stamping. The stamping operation is carried out along a longitudinal side of the lamella, into which the desired blade shape is impressed along the longitudinal side. In this way, a cutting edge that is not excessively sharp, but rather rounded and, in particular, uniform and symmetric on both sides can be rationally produced.

The inventive welding knives are stored in a box that preferably can be exchanged as a whole.

BRIEF DESCRIPTION OF THE FIGURES

An exemplary embodiment of the invention is described in greater detail below with reference to the drawings. In these drawings:

FIG. 2 shows a bottom view of the inventive device, FIG. 11 shows the vertical and horizontal temperature distribution on the welding knife along a first, second and third line.

In the different figures, identical components are identified by the same reference symbols. Identical components, which are illustrated a number of times, are respectively identified by a reference symbol only once.

DETAILED DESCRIPTION OF THE PRESENT INVENTION

Figure 1:
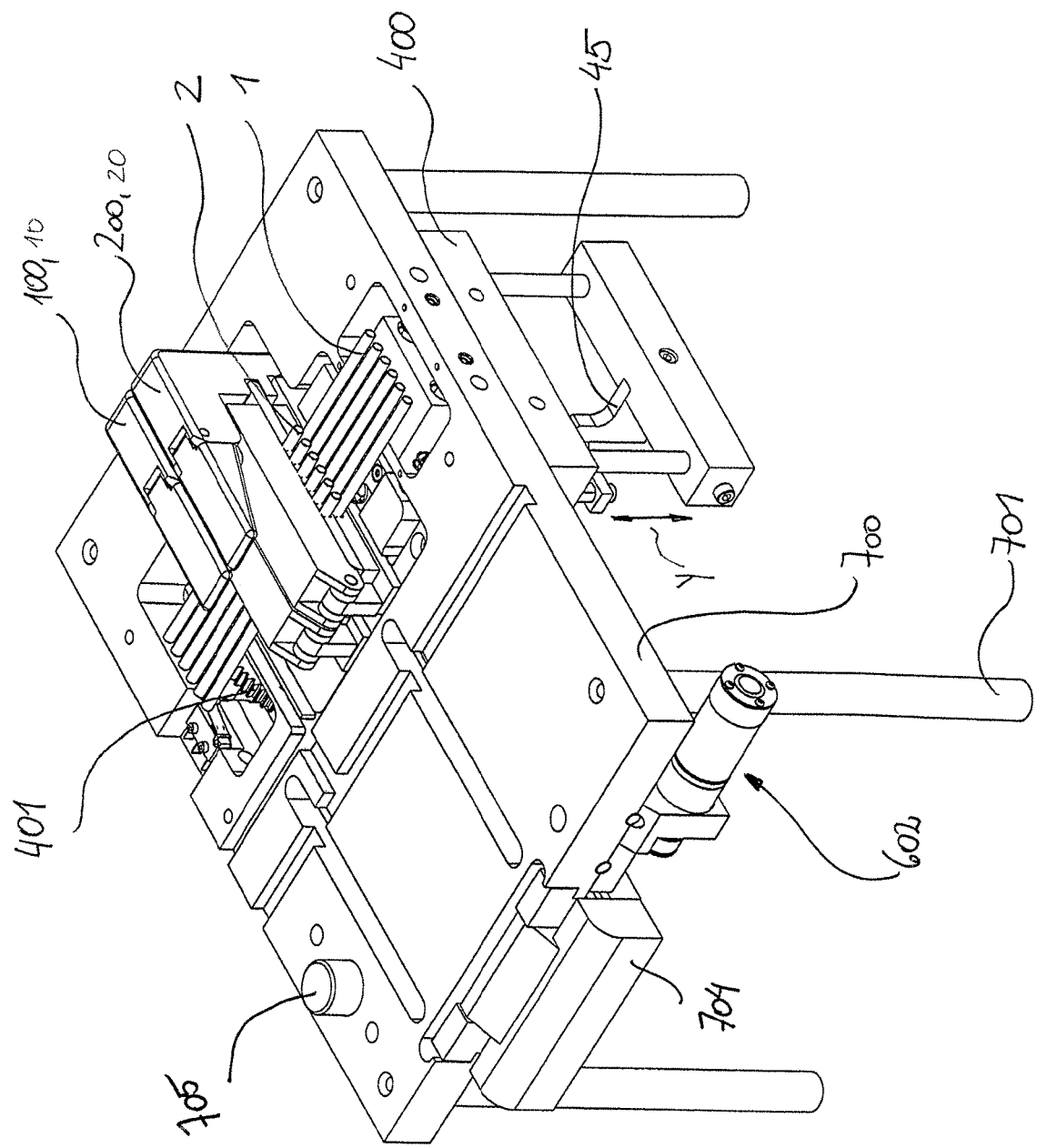
FIG. 1 shows a perspective representation of the inventive device with table and table legs in the form of an oblique view from above.

FIG. 1 shows a perspective top view of the inventive device according to the exemplary embodiment, which is assembled on a table 700. The table stands on four legs 701. The device comprises two tube holders 100, 200, into which tubes are inserted, wherein the tubes of a first group of tubes 1 extend on a first plane and the tubes of a second group of tubes 2 extend on a second plane that lies above the first plane. The two tube holders 100, 200 additionally comprise clamping levers 10, 20.

Figure 1A:
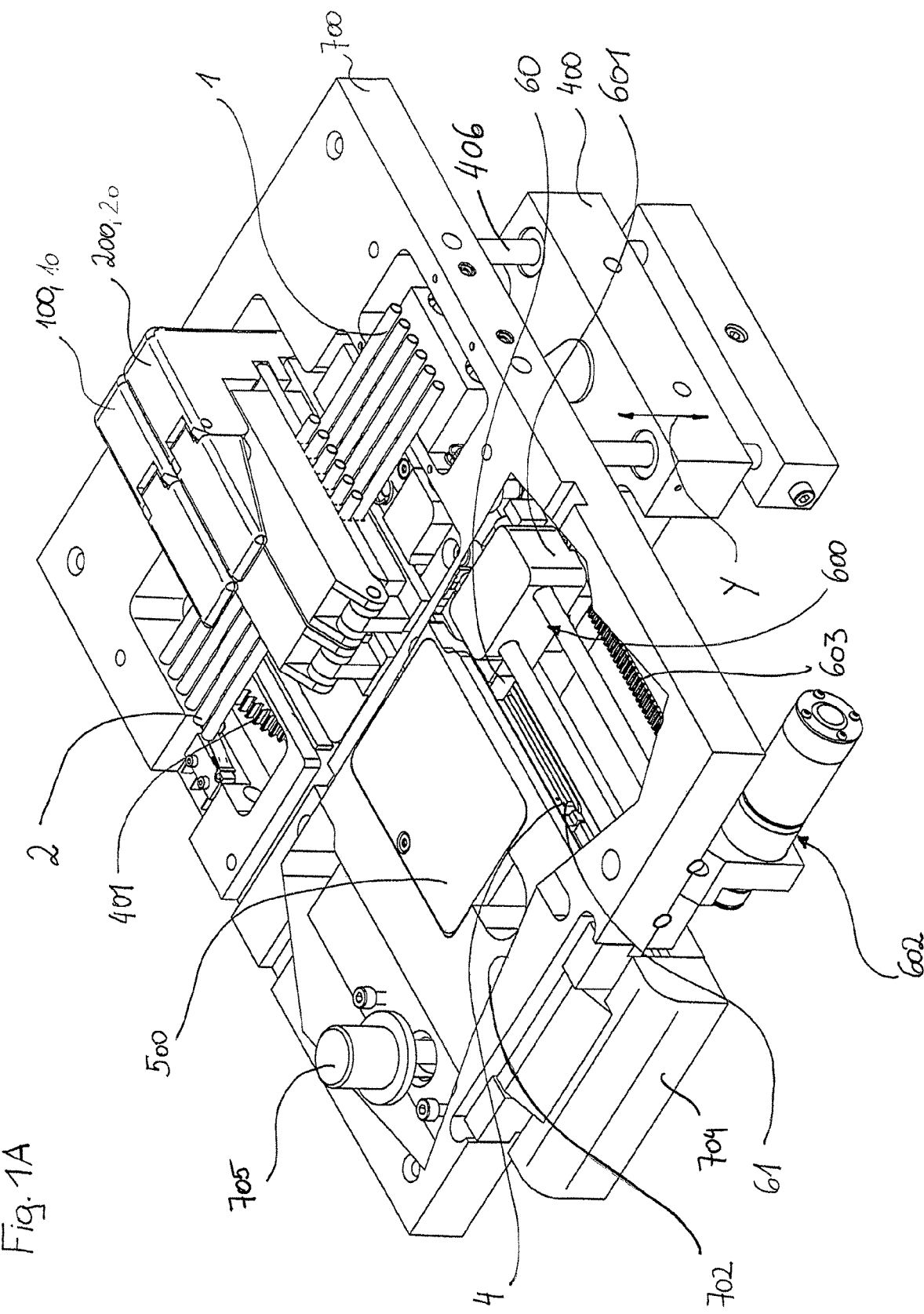
FIG. 1A shows a perspective top view of the inventive device with closed tube holders and inserted tubes.

In FIG. 1A, a box 500, in which welding knives are stored, and a welding knife feed 600 to a welding knife holder 40 are visible through a cutout 702 in the table 700 produced for this purpose. The welding knife holder is arranged underneath the tube holders 100, 200 such that it is not visible in FIGS. 1 and 1A. The welding knife feed 600 comprises a transport carriage 601 for a slide 60 and a drive unit 602 that consists, for example, of a "DC planetary gear brush motor." The slide 60 is connected to the drive unit 602 by means of a synchronous belt 603. The box 500 is designed in such a way that the individual welding knives 4 are sorted in the box 500 extending in the longitudinal direction (not visible in FIG. 1). The box 500 is open on the side that is directed toward the welding knife feed 600. A spring element (not visible in FIG. 1) is arranged in the box and presses the welding knife 4 intended for the next welding operation into the guide rails 61 of the welding knife feed 600.

The welding knife holder 40 (not visible in FIG. 1) is mounted on a platform 400 arranged underneath the table 700. An additional drive unit 401 is provided for moving the platform 400 and the welding knife holder 40 toward or away from the table 700 (arrow Y), i.e. vertically up and down if the table is aligned horizontally.

The illustration of an additionally provided housing is omitted in FIG. 1 and in the other figures. The tube holders 100, 200 preferably protrude upward from the housing such that the housing does not have to be opened in order to insert or remove the tubes. In addition, the box 500 with the welding knife supply should be easily accessible in order to be exchanged, wherein this is realized with the aid of a drawer 704. Control elements such as a start button 705 may likewise be provided on the housing (see, for example, FIGS. 1, 1A).

FIG. 2 shows the inventive device in the form of a bottom view, wherein the platform 400, on which the welding knife holder 40 is mounted, and additional components of the drive unit 401 for moving the platform 400 in a vertical direction are visible in this figure. This drive unit comprises three gearwheels 402, 403 and 407, wherein the gearwheel 402 is connected to the platform 400 by means of a connecting rod 405. The gearwheel 407 is located between the gearwheels 402 and 403 (visible in FIG. 2). The connecting rod 405 converts the circular motion of the gearwheel 402 into a linear up and down motion of the platform 400 along rod-shaped guides 406. The gearwheel 403 is driven by a motor 404 that, for example, once again consists of a "DC planetary gear brush motor." FIG. 2 also shows a transformer unit 90 for heating the welding knife 4, which is described in greater detail further below.

Figure 3:
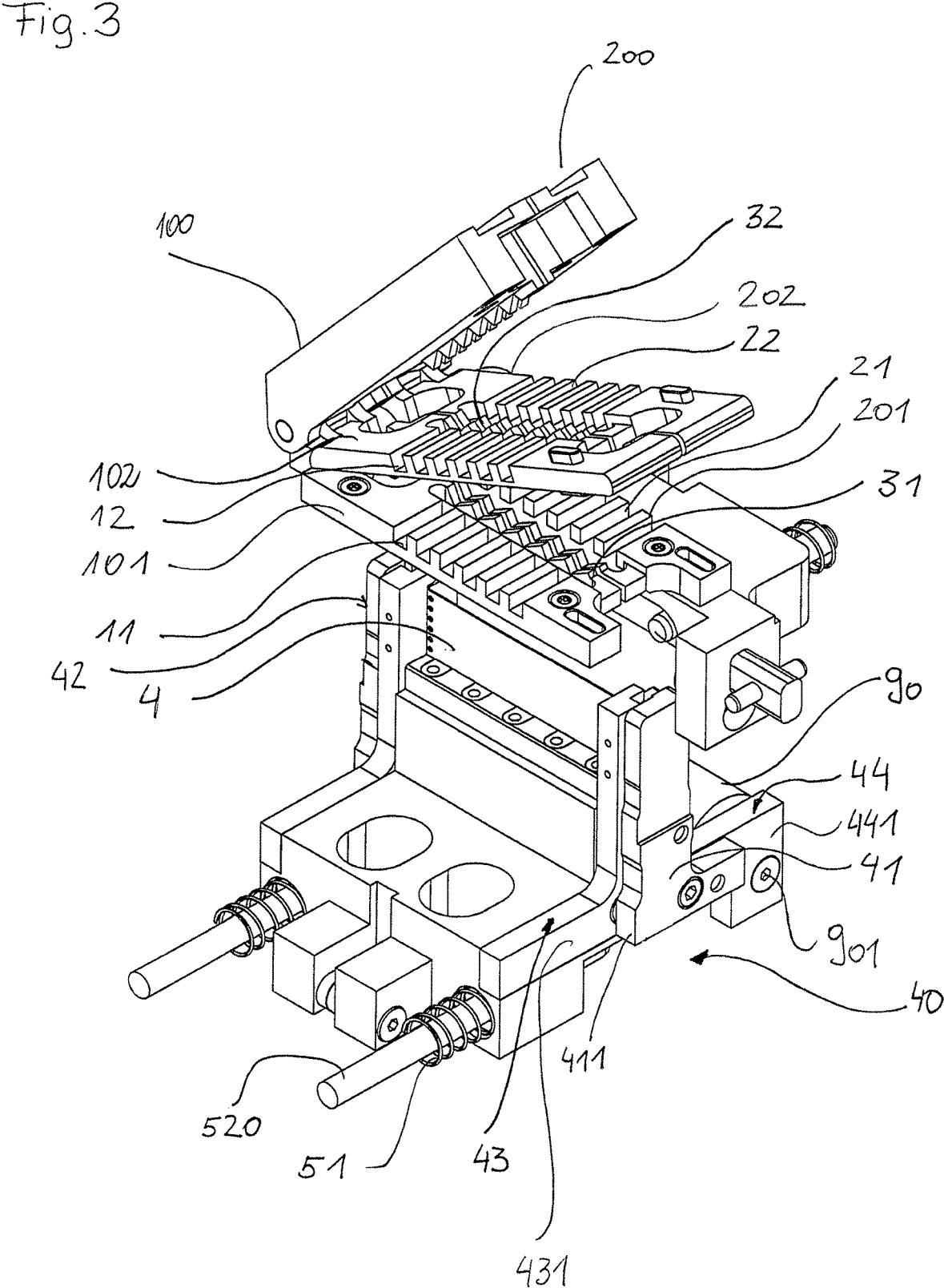
FIG. 3 shows part of the inventive device in the form of a perspective view with open tube holders.

FIG. 3 shows part of the inventive device in the form of a perspective view, in which the tube holders 100, 200 are open and no tubes are inserted therein. The first and the second tube holder 100, 200 respectively comprise a first tube clamp 101, 201 and a second tube clamp 102, 202. The first tube clamp 101 of the first tube holder 100 and the first tube clamp 201 of the second tube holder 200 respectively comprise a lower part and an upper part. The second tube clamp 102 of the first tube holder 100 and the second tube clamp 202 of the second tube holder 200 also respectively comprise a lower part and an upper part. The upper part of the first tube clamp 101 of the first tube holder 100 and the upper part of the first tube clamp 201 of the second tube holder 200 simultaneously form the lower part of the second tube clamps 102, 202 of the first and the second tube holder 100, 200. Each tube clamp comprises through-openings 11, 12, 21 and 22, into which the tubes of a first and a second group of tubes are inserted. The through-openings 11, 21 of the two first tube clamps 101, 201 are arranged on a first plane and the through-openings 12, 22 are arranged on a second plane. The first plane extends parallel to the second plane and is vertically spaced apart therefrom. The two first tube clamps 101, 201, as well as the two second tube clamps 102, 202, comprise first and second squeezing zones 31, 32 that are provided for squeezing the inserted tubes before they are severed. The squeezing zones 31, 32 are realized in a sawtooth-shaped manner such that the tubes are squeezed at an oblique angle, particularly an angle of 25°-30°. The squeezed tubes are completely closed such that any liquid contained in the tubes, e.g. donor blood, can no longer pass the squeezing zones.

FIG. 3 furthermore shows the welding knife holder 40 with its first clamping part 43, which is arranged opposite of a second clamping part 44 and can be moved relative to this second, stationary clamping part along rod-shaped guides 520. Both clamping parts respectively comprise a pair of angled clamping arms 431, 441, wherein the welding knife 4 is held between the upwardly protruding sections of these clamping arms. First springs 51 are used for pressing the first clamping part 43 against the second clamping part 44.

A pair of crank brackets 41 is mounted on the clamping part 44, wherein a total of four first cranks 411 are formed on both sides of the upwardly protruding sections of said crank brackets. Alternatively, the clamping part 44 and the pair of crank brackets 41 are realized in one piece. The cranks 411 are identical to one another and arranged mirror-symmetrical to the plane of the welding knife 4 when the welding knife is clamped between the clamping parts 43, 44. Furthermore, the rear crank bracket 41 in FIG. 3 is provided with a slot 42 for inserting the welding knife 4 between the two clamping parts 43, 44 (not visible in FIG. 3).

FIG. 3 also shows additional components of a heater for the welding knife 4, which comprises the aforementioned transformer unit 90. A primary winding in the form of multiple copper wire windings, for example, 5-15 windings, is wound around a hollow-cylindrical ferrite core of this unit over the circumference thereof, wherein the individual windings essentially extend in the axial direction of the ferrite core, as well as through this ferrite core. On the other hand, the secondary winding is formed by only one individual conductor, which extends through the ferrite core in a straight manner and the ends of which are respectively screwed to the lower sections of the clamping arms 441 of the clamping part 44 (screw 901). The clamping arms 441 are electrically conductive and form part of the secondary circuit, which is closed by the electrically conductive welding knife 4 as soon as this welding knife is clamped between the first clamping part 43 and the second clamping part 44 and in contact with the clamping arms 441. Since the welding knife 4 has a significantly smaller cross section and a higher specific resistance than the straight conductor forming the secondary winding and the two clamping arms 441, its electrical resistance is comparatively high such that the majority of the electrical power loss of the secondary circuit occurs in the welding knife. In addition, the transformation ratio of the transformer unit 90 with only one winding in the secondary circuit results in a higher secondary current such that the welding knife can be very effectively and quickly heated to the desired temperature of about 300° C. within 3 to 4 seconds. In this case, currents in excess of 100 A can be reached.

Figure 4:
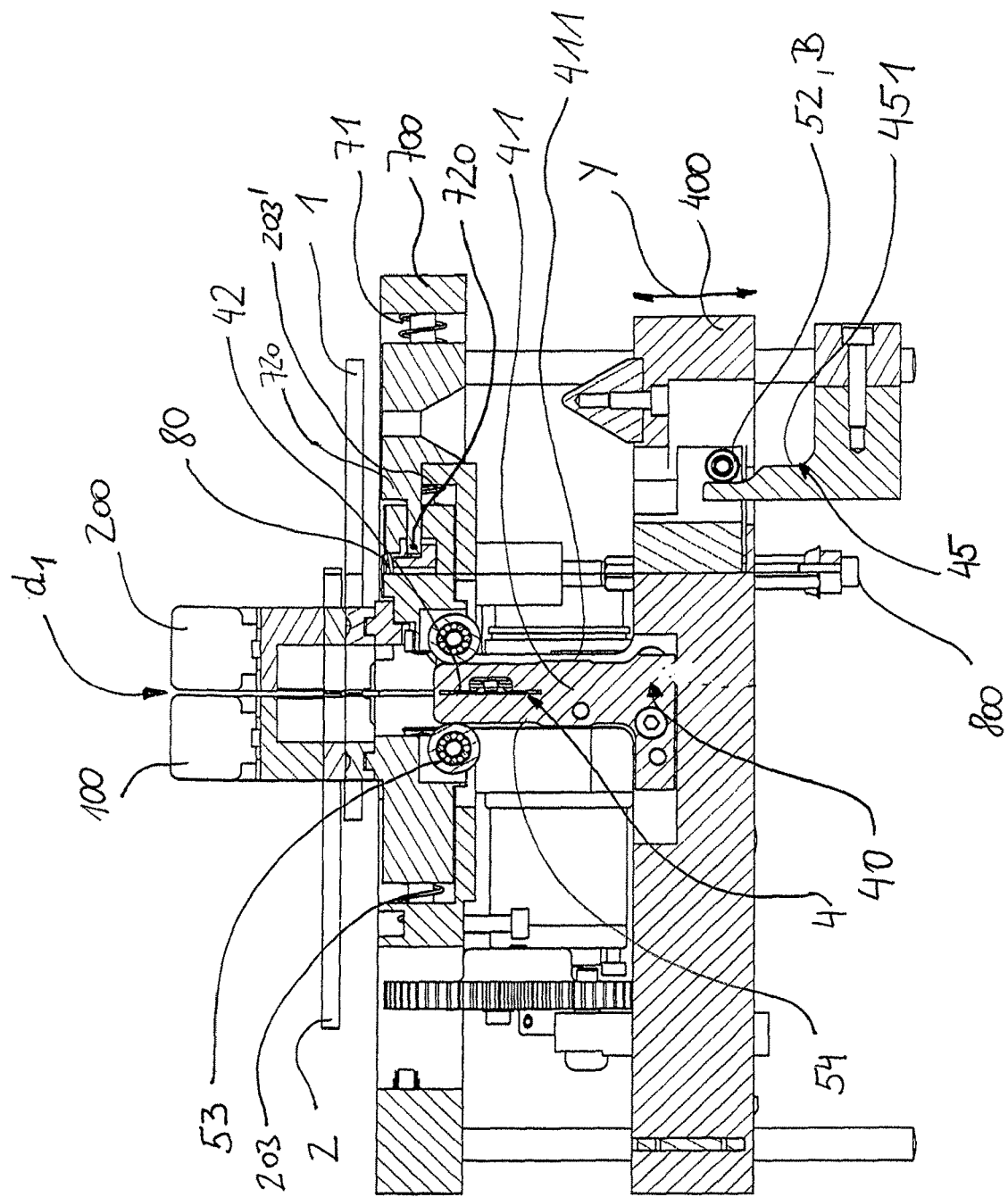
FIG. 4 shows a sectional representation of the inventive device, wherein the welding knife holder is in a position, in which the welding knife can be received ("blade feed position")

FIG. 4 shows a sectional representation of the inventive device, in which the platform 400 and therefore the welding knife holder 40, which can be moved relative to the table 700 in the vertical direction along the arrow Y, are in the so-called "blade feed position." In this position, the welding knife holder 40 is located at such a height that the welding knife 4 can be inserted through the slot 42 between the two clamping parts 43, 44. The two clamping parts 43, 44 are slightly spaced apart from one another for this purpose. The distance between the two clamping parts 43, 44 is adjusted against the force of the springs 51 by tracing a second crank 451 on a second crank bracket 45 with the aid of a tracer wheel 52. In the "blade feed position," the tracer wheel 52 on the second crank 451 is in a pickup position (B), in which the two clamping parts 43, 44 are spaced apart from one another by no more than the distance required for the insertion of the welding knife 40.

The two tube holders 100, 200 are respectively mounted in the table 700 in a displaceable manner and therefore not only can be moved relative to one another, but also jointly in the same direction. They are prestressed relative to one another by means of second springs. In FIG. 4, the corresponding second springs are identified by the reference symbols 203, 203'. Furthermore, a pair of tracer wheels 53 is respectively mounted on the tube holders 100, 200. This results in a total of four tracer wheels 53, which cooperate with the aforementioned four first cranks 411 on the crank brackets 41 when these crank brackets engage between the pairs of tracer wheels 53 as it is the case in the "blade feed position" illustrated in FIG. 4. The horizontal distance d1 is adjusted between the two tube holders 100, 200 by tracing the four first cranks 411. In the "blade feed position" illustrated in FIG. 4, the first and the second tube holder 100, 200 are spaced apart from one another by the distance d1. Since the four first cranks 411 are realized identical to one another and mirror-symmetrical to the plane of the welding knife 4 and the two tube holders 100, 200 can be jointly displaced in the same direction, the tube holders 100, 200 are always aligned relative to the welding knife holder 40 in such a way that the welding knife is located exactly in the center between the two tube holders 100, 200. Any tolerances between the platform 400 carrying the welding knife holder 40 and the table 700, on which the tube holders 100, 200 are mounted, are thereby compensated.

Figure 4A:
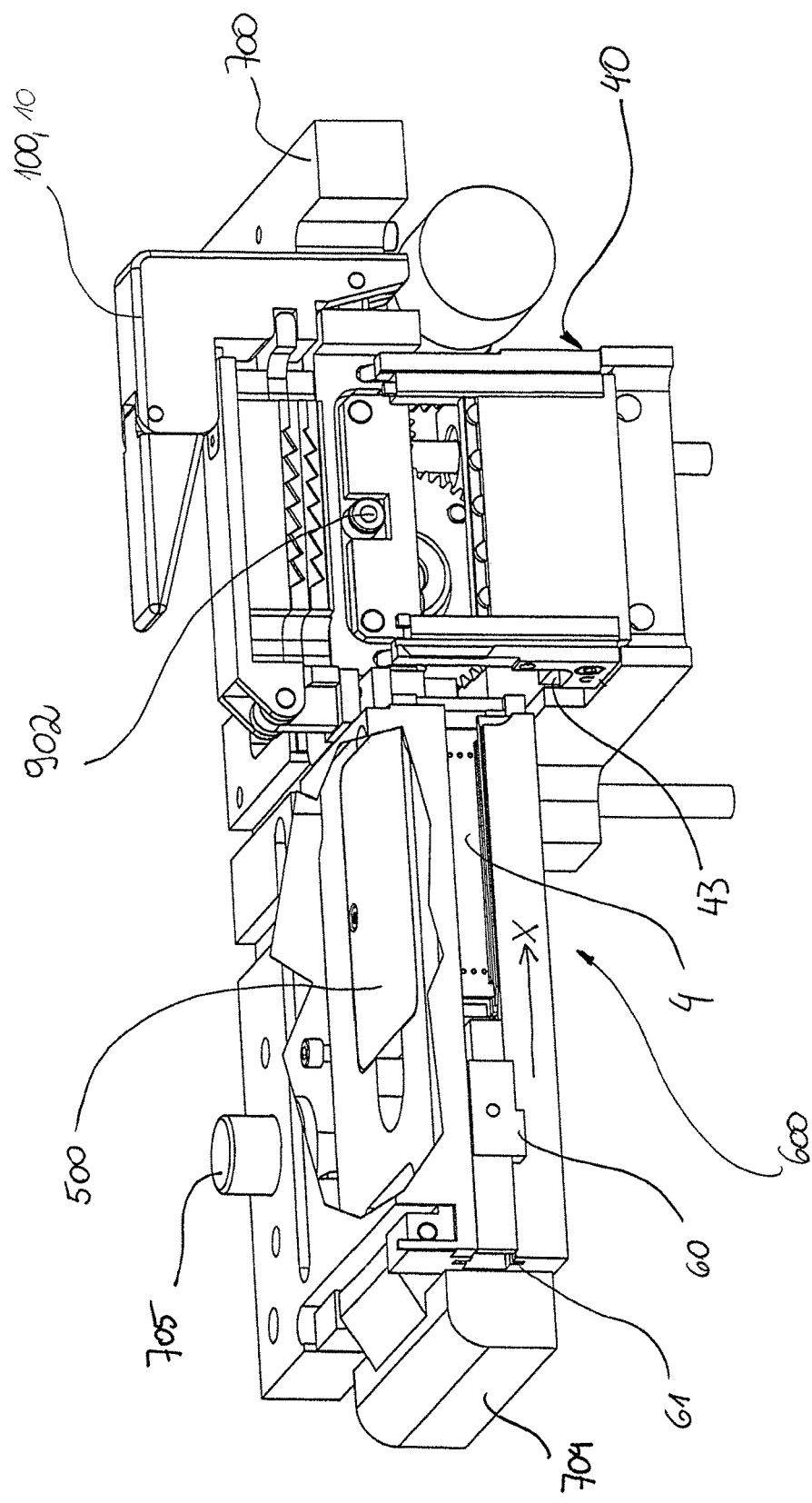
FIG. 4A shows the inventive device in the "blade pickup position," wherein a few components were omitted in order to provide a clear view of the welding knife feed and one of the welding knife holders.

FIG. 4A shows part of the inventive device. This figure specifically shows one of the two tube holders 100 that is arranged on the table 700 and comprises the clamping lever 10. The second half of the device, which comprises the second tube holder 200 and the second clamping part 44, is omitted in FIG. 4A. The welding knife holder 40 with the first clamping part 43 is therefore partially visible. The welding knife holder 40 is in the "blade feed position" as described above with reference to FIG. 4. The tubes of the first and second group of tubes 1, 2 should, in principle, already be inserted into the device in this position, but are likewise omitted in FIG. 4. The welding knife feed 600 comprises the slide 60, which is moved along the guide rails 61 with the carriage 601 and driven by means of an additional drive unit 602 (see FIG. 1A). In order to insert the welding knife 4 into the welding knife holder 40, the slide 60 is moved in the direction of the arrow X and in the process carries along the welding knife 4. A new welding knife is inserted for each welding operation such that each welding knife 4 is only used once. A large number of welding knives 4 is stored in the box 500. The box 500 is designed in such a way that one welding knife 4 is respectively pushed forward into the region of the guide rails 61 for each welding operation, namely such that the welding knife can be picked up by the slide 60 and displaced into the welding knife holder 40. FIG. 4A also shows a temperature sensor 902, by means of which the temperature of the welding knife is detected and controlled.

Figure 4B:
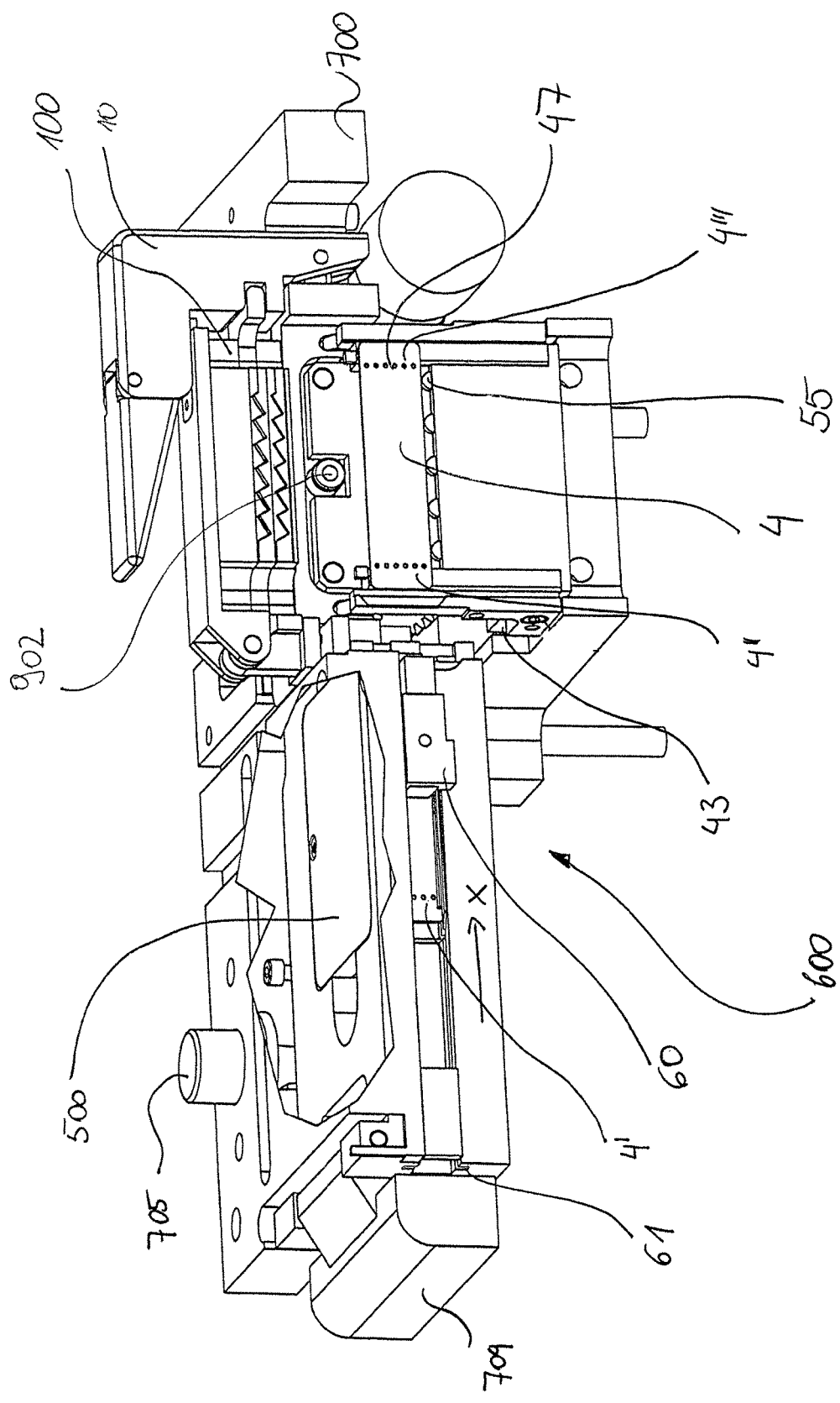
FIG. 4B shows the partial illustration according to FIG. 4A at the time, at which the welding knife is inserted into the welding knife holder.

FIG. 4B shows the partial illustration according to FIG. 4A, in which the welding knife 4 is inserted into the welding knife holder 40. Another welding knife 4' is already prepositioned for the next welding operation. The welding knife 4 is guided in the welding knife holder 40 on crescent-shaped rails 55. In order to completely insert the welding knife 4, the slide 60 itself engages into the welding knife holder 40 by a certain distance. It is therefore initially required to once again retract the slide 60 from the region of the welding knife holder 40 by reversing its moving direction before the additional steps, which include a vertical displacement of the welding knife holder 40 from of the "blade feed position," can be carried out. FIG. 4B shows the slide 60 in a position, in which it has already been retracted again by a certain distance.

FIG. 4B shows a preferred embodiment of the welding knife 4. Peripheral zones 4" and 4'" extend along its two shorter sides of the rectangle. In the inserted state, these peripheral zones 4" and 4'" are contacted by the first and the second clamping part 43, 44 (not visible). In order to ensure a sound electrical contact, the clamping part 44 comprises projecting contact points, preferably in the form of spring-mounted pressure pads, on the inner side of the upwardly protruding sections of the clamping arms 441. In the vicinity of its peripheral zones, the welding knife 4 comprises recesses 48 that are realized in the form of bores along the two shorter rectangle sides. The welding knife 4 punctually rests on the crescent-shaped rails 55 along its lower rectangle side.

Figure 5:
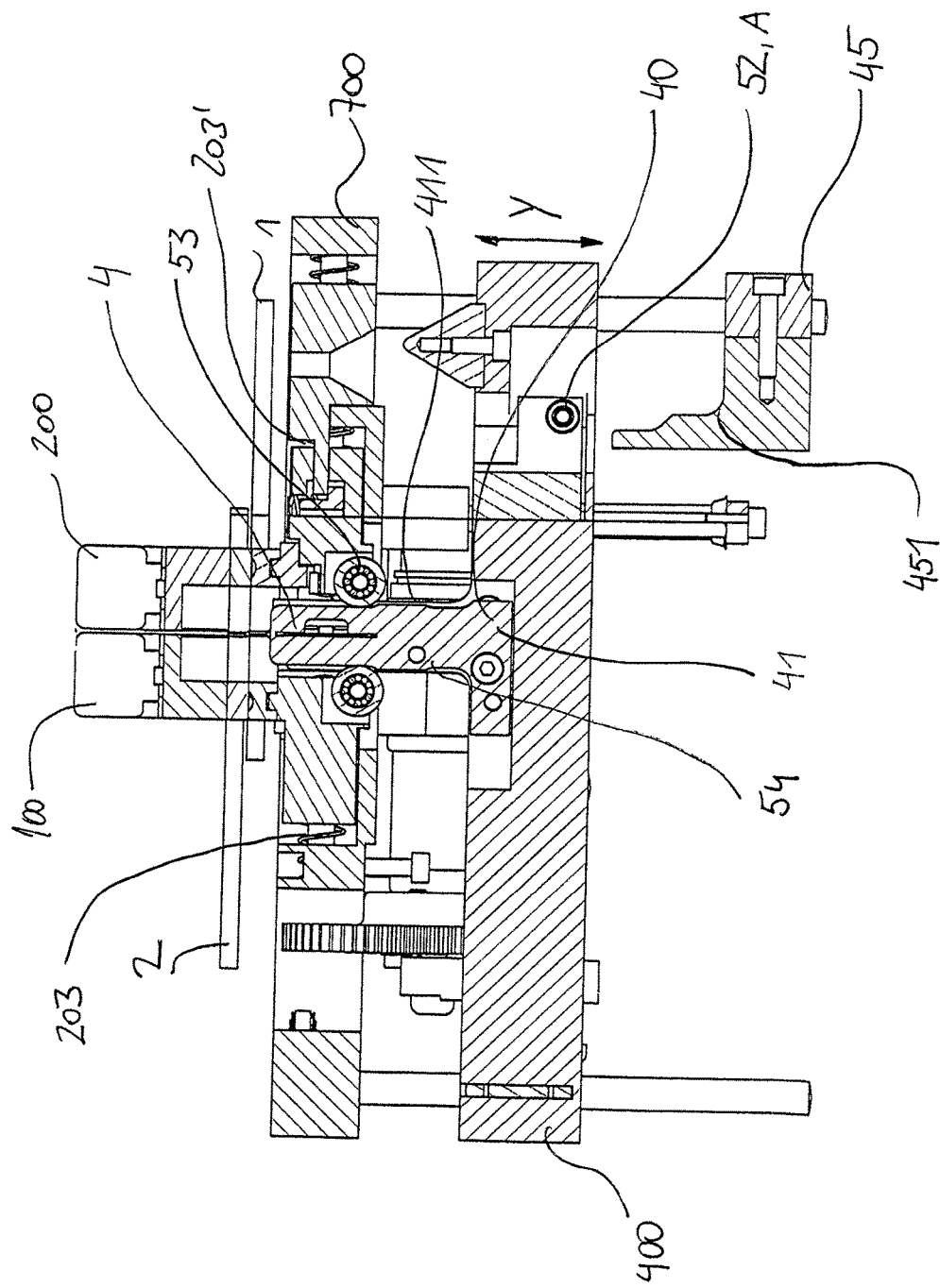
FIG. 5 shows a sectional representation of the inventive device in a position, in which the welding knife is inserted into the welding knife holder and electrically contacted ("pre-cut position")

FIG. 5 shows a sectional representation of the inventive device, wherein the platform 400, by means of which the welding knife holder 40 is moved in the vertical direction along the arrow Y, is in the so-called "pre-cut position." In comparison with the "blade feed position" illustrated in FIG. 4, the platform 400 has been displaced upward by a certain distance. In this position, the tracer wheel 52 above the second crank bracket 45 is disengaged from the second crank 451 and in a so-called contacting position (A). In this position, the two clamping parts 43, 44 are no longer spaced apart from one another by the second crank 451, but rather can now clamp the welding knife 4 between one another, wherein the welding knife is at the same time electrically contacted. The welding knife 4 is then also electrically heated in this position.

Figure 6:
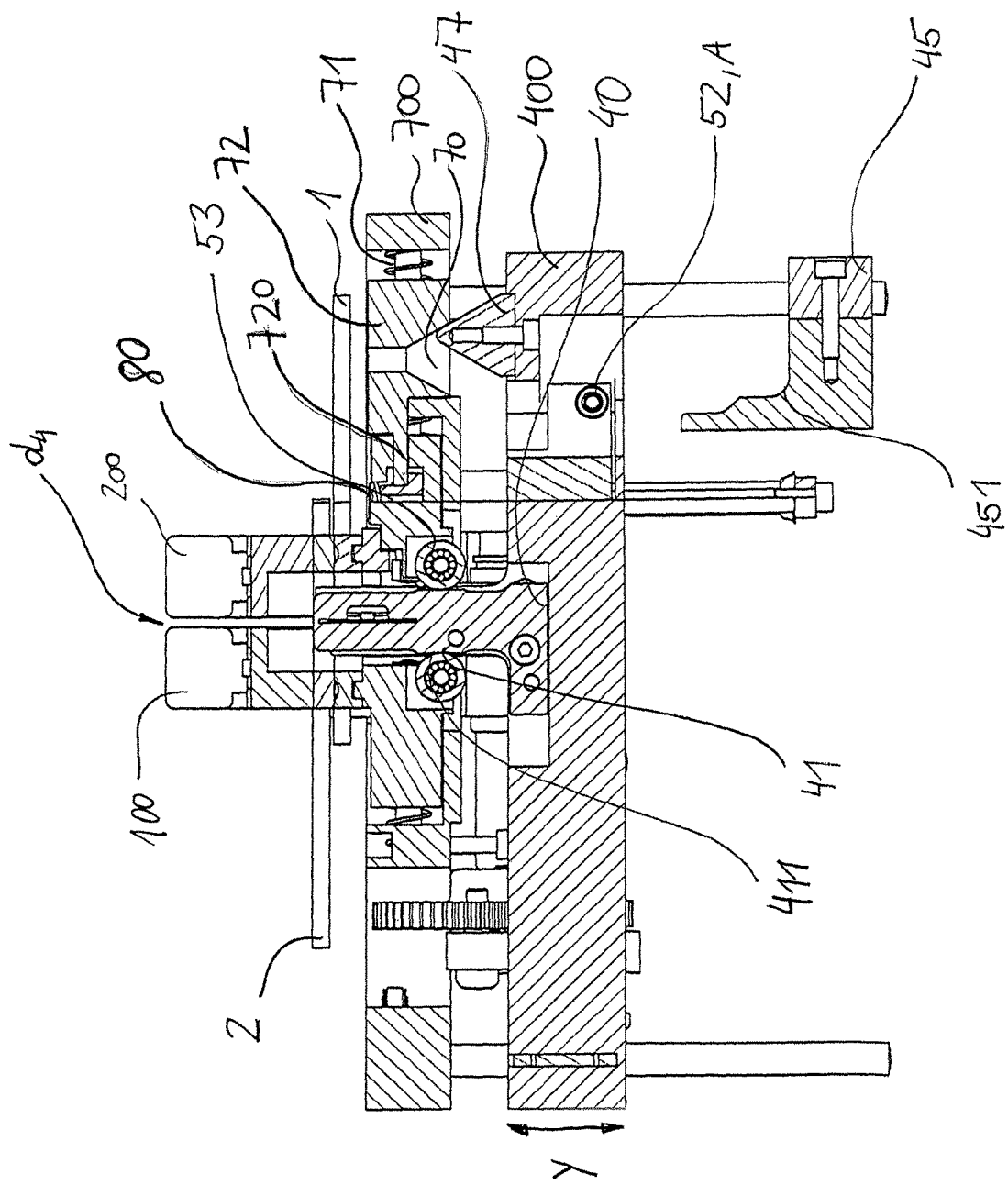
FIG. 6 shows a sectional representation of the inventive device in a position, in which the first and the second tube holder are spaced apart from one another in such a way that the inserted tubes are stretched ("stretch position")

FIG. 6 shows a sectional representation of the inventive device, wherein the platform 400, by means of which the welding knife holder 40 is moved in the vertical direction along the arrow Y, is in the so-called "stretch position." In comparison with FIG. 4 and FIG. 5, the platform 400 has been additionally displaced in the direction of the table 700 and the tracer wheels 53 are now in a position on the first cranks 411, in which the distance between the two tube holders 100, 200 is adjusted to its maximum value d4. The tubes of the first and the second group of tubes 1, 2 are thereby stretched. The first cranks 411 on the crank brackets 41 are designed in such a way that this distance d4 is preserved during the subsequent additional motion of the platform 400 in the direction of the table 700, in the course of which the cutting knife 4 severs the tubes. The tubes are thereby severed in the stretched state.

Figure 7:
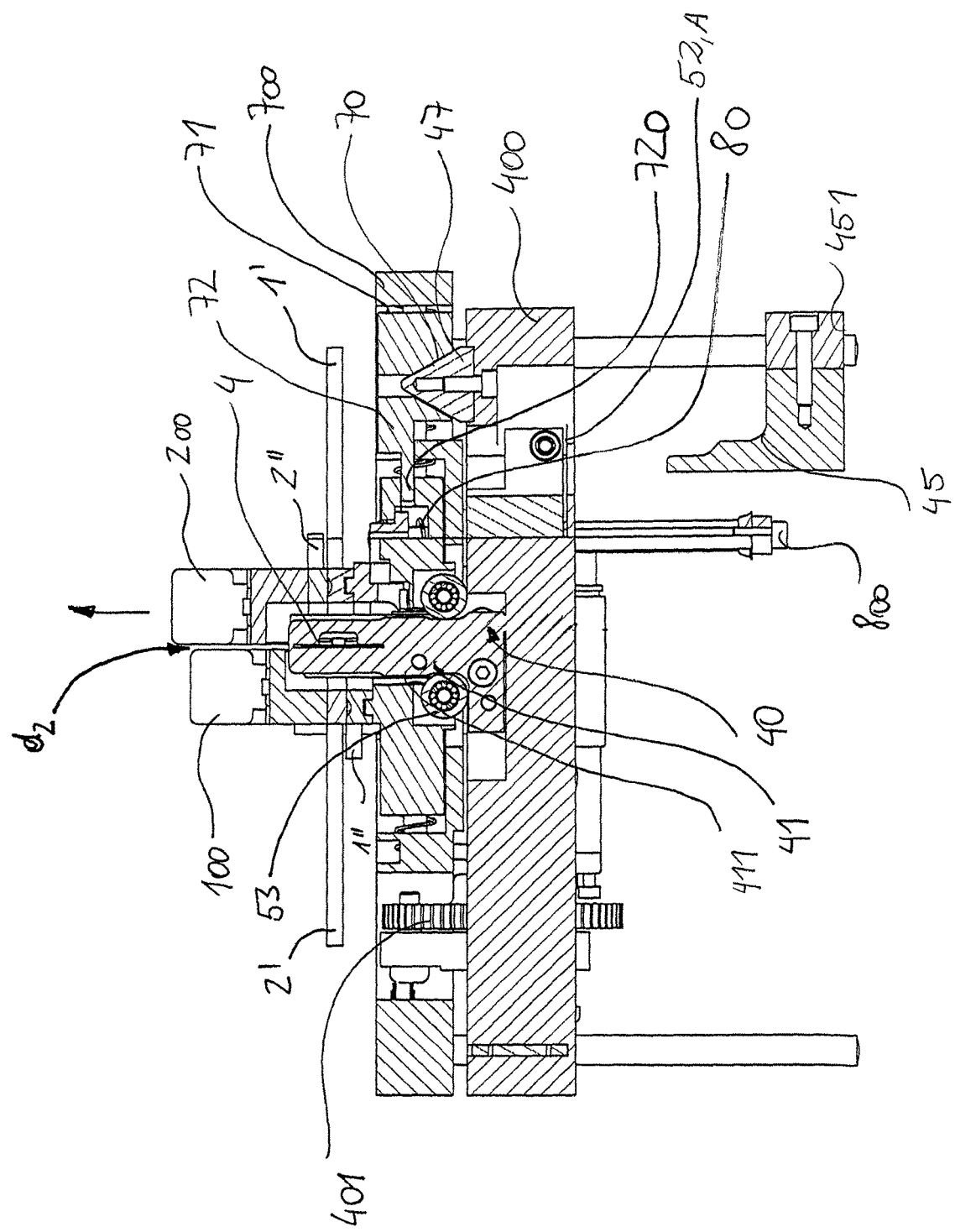
FIG. 7 shows a sectional representation of the inventive device in a position, in which the tubes are severed by the welding knife, wherein the first and the second tube holder are vertically displaced relative to one another and the tubes are aligned with one another ("cut position")

FIG. 7 shows a sectional representation of the inventive device, in which the platform 400 is in the so-called "cut position," wherein the tubes of the first and the second group of tubes 1, 2 are severed in this position.

The cut ends 1' of the tubes of the first group of tubes have to be vertically aligned with the cut ends 2' of the tubes of the second group of tubes immediately after the tubes have been severed. For this purpose, the second tube holder 200 can be vertically displaced and is upwardly prestressed by means of a third spring 80. However, this motion of the second tube holder 20 is blocked in the positions described so far due to the engagement of a stopping face 720 on a latch 72, which can be horizontally displaced in the table 700 and is prestressed relative to the second tube holder by means of a fourth spring 71. The stopping face 720 is retracted in order to thereby unlatch the second tube holder 200 due to the engagement of a cone 47 arranged on the platform 400 into a hollow cone 70 arranged eccentric thereto on the underside of the latch 72. The fourth spring 71 is thereby compressed. According to FIG. 6, the cone 47 already begins to engage into the hollow cone 70 in the "stretch position." The cone 47 and the hollow cone 70 are adapted to one another in such a way that the second tube holder 200 is unlatched during the vertical motion of the platform 400 as soon as the tubes of both groups of tubes 1, 2 are completely severed. The third spring 80 presses the second tube holder 200 upward after it has been unlatched.

According to FIG. 7, the cone 47 has completely engaged into the hollow cone 70 in the "cut position" and thereby unlatched the second tube holder 200 such that it can be displaced upward by the third spring 80. In this way, the cut ends 1' of the tubes of the first group of tubes are vertically aligned with the cut ends 2' of the tubes of the second group of tubes. The welding knife 4 is still located between the tubes.

The platform 400 has reached its highest position in the "cut position." The tracer wheel 52 of the second crank 451 is still located on top thereof in the contacting position (A) such that the welding knife 4 is clamped between the clamping parts 43, 44 and can be/is heated. The tracer wheels 53 on the first cranks 411 adjust the distance between the tube holders 100, 200 to the distance d2, which is dimensioned such that the cut ends 1' and 2', as well as the residual ends 1", 2", are pressed against the hot welding knife 4 and thereby molten.

The welding knife 4 is subsequently retracted from the region of the cut tubes. This is achieved in that the platform 400 and therefore the welding knife holder 40 are now moved downward. The reversal of their moving direction is realized automatically by means of the connecting rod 405 without reversing the rotating direction of the motor 404 of the drive unit 401. In the process, the tracer wheels 53 on the first cranks 411 initially once again pass the region, over which they have already traveled during the "stretch position" and in which the distance between the two tube holders 100, 200 is adjusted to its maximum value d4. In this way, the tubes with the molten ends are slightly moved away from the welding knife 4 in order to thereby simplify its retraction. Furthermore, the molten material located on the molten ends is not transported away due to the retraction and therefore available for the subsequent welding operation.

Figure 8:
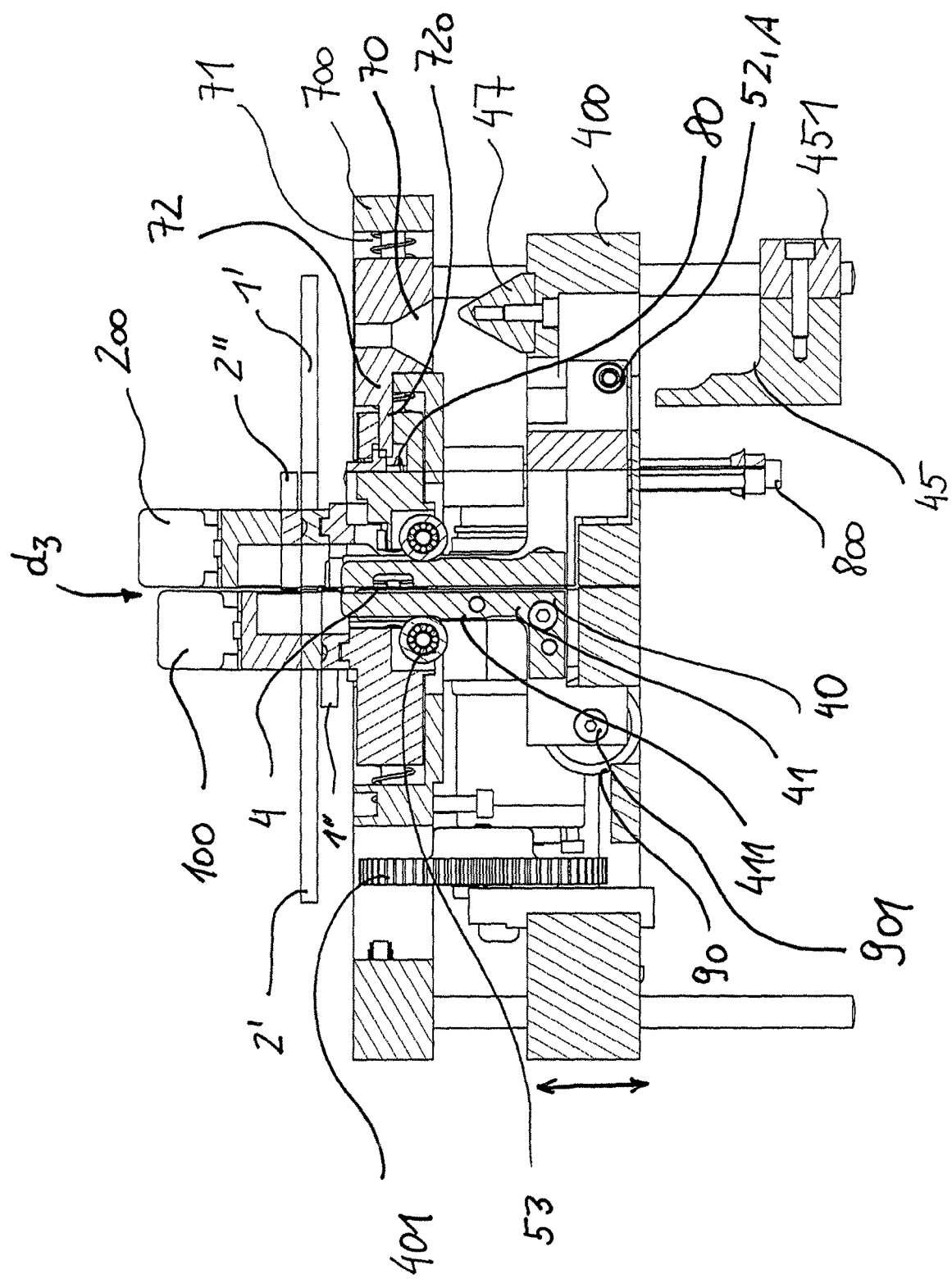
FIG. 8 shows another sectional representation of the embodiment with inserted tubes, in which the first and second tube holder are vertically displaced relative to one another and the tube ends to be welded are aligned with one another and joined ("press position"), wherein the welding knife is no longer located between the tube holders.

During the further downward motion of the platform 400, the tracer wheels 53 on the first cranks 411 once again reach the region, over which they have traveled during the "precut position" and in which the distance between the two tube holders 100, 200 is adjusted to the smaller value d3. As a result, each cut end 1' of the first group of tubes is respectively contacted with a cut end 2' of the second group of tubes and respectively welded into a continuous tube. This so-called "press position" is illustrated in FIG. 8. In the "press position" according to FIG. 8, the platform 400 stops such that the joined tubes, as well as the residual ends 1", 2", can be removed from the device after a certain cooling period.

Figure 9:
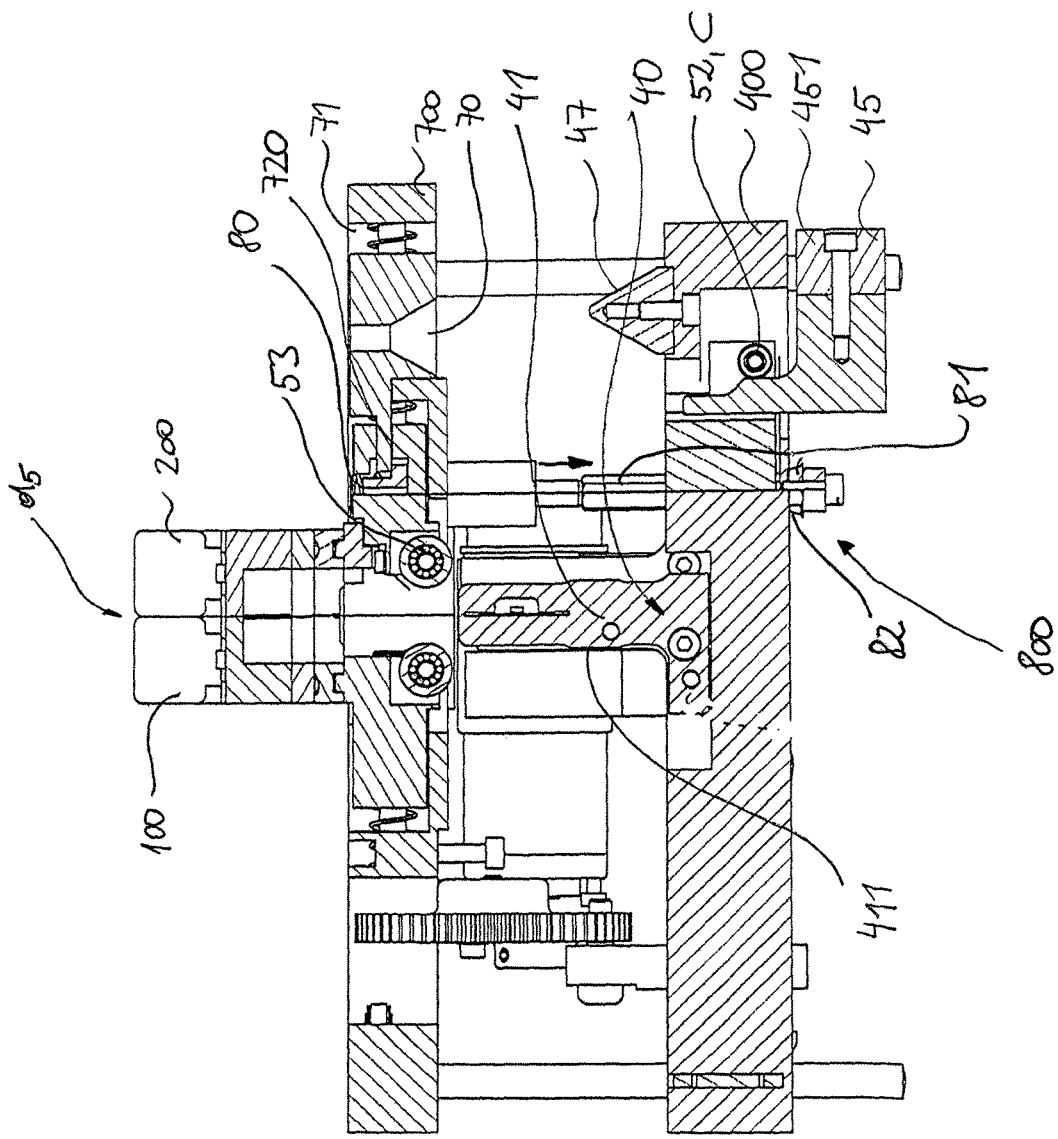
FIG. 9 shows a sectional representation of the inventive device in a position, in which the welding knife is ejected ("eject position")

FIG. 9 shows a sectional representation of the inventive device, in which the platform 400 and the welding knife holder 40 are in the "eject position." The platform 400 has reached its lowest position in the "eject position." The welded tubes and the residual ends have already been removed from the tube holders 100, 200. As mentioned above with reference to FIG. 4, the distance between the two clamping parts 43, 44 is adjusted by tracing the second crank 451 with the aid of a tracer wheel 52. When the welding knife holder 40 is in the "eject position," the tracer wheel 52 of the second crank 451 is in a release position (C). In this case, the first clamping part 43 has been moved relative to the second clamping part 44 against the force of the first spring 51 (not visible in FIG. 9) in such a way that the gap width between the two clamping parts 43, 44 is adjusted to its maximum. The welding knife 4 is thereby released and can drop down from the welding knife holder 40 into a disposal box (not illustrated in FIG. 9).

During the transition from the "press position" according to FIG. 8 into the "eject position" according to FIG. 9, the second tube holder 200 is moved back from its upwardly displaced position into its starting position, in which it is arranged at the same height as the first tube holder 100. The third spring 80 is simultaneously tensioned. This is realized by means of a return motion mechanism 800 with a tie rod 81 that is coupled to the second tube holder 200. As the platform 400 moves downward, it comes in contact with a stop 82 of the tie rod 81 and the pulls this tie rod along during its downward motion. The cone 47 is in the process also disengaged from the hollow cone 70 such that the stopping face 720 once again engages into the second tube holder 200. The second tube holder is in its starting position, in which it is arranged at the same height as the first tube holder 100.

During the downward motion into the "eject position," the tracer wheels 53 are ultimately also disengaged from the first cranks 411 on the crank brackets 41. The distance between the two tube holders 100, 200 is in the process reduced to such a degree that the tube holders 100, 200 contact one another.

Figure 10:
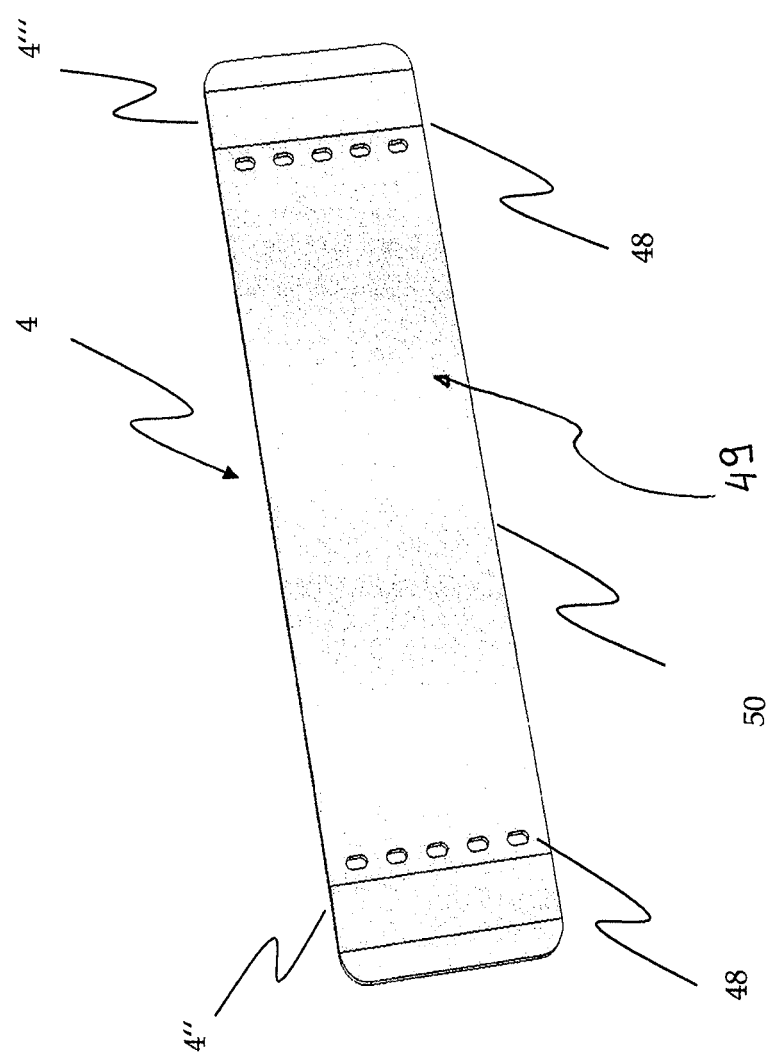
FIG. 10A shows a preferred embodiment of a welding knife.

FIG. 10 shows the preferred embodiment of the welding knife 4 with a rectangular shape, wherein recesses 48 are respectively arranged in a row along the peripheral zones 4", 4'" of the two shorter rectangle sides. The welding knife 4 is preferably produced by longitudinally folding a lamella of double width in half. In this case, the bending edge, along which the two halves of the lamella are connected to one another, serves as the blade 50 for cutting the tubes. As an alternative to this folded design, the welding knife 4 may be produced by means of punching and its blade 50 may be produced by means of stamping. In this way, a cutting edge that is not excessively sharp, but rather rounded and, in particular, uniform and symmetric on both sides, can be rationally produced. The latter is important for preventing the cutting knife from being deflected toward one side while the tubes are severed as it would be the case, for example, with an asymmetrically ground edge.

The blade 50 for cutting the tubes extends along one of the two longer rectangle sides.

For example, the welding knife 4 has a length between 60-80 mm, particularly 70 mm, a width between 15-20 mm, particularly 17 mm, and a thickness between 0.2-0.5 mm, particularly 0.3 mm. The size of the melting surface 49 primarily depends on the diameter of the tubes and on the number of tubes to be welded.

The material used for the welding knife 4 consists, for example, of chrome/nickel steel.

The horizontal and the vertical temperature distribution over the surface of the welding knife are relevant for a high-quality welding result. It was determined that the arrangement of the recesses along the peripheral zones 4", 4' leads to a more homogenous vertical heat distribution. The desired temperature of the welding knife amounts to about 300° C.

FIG. 11 shows another embodiment of a welding knife 56. For example, six recesses 57 with a preferably circular shape are respectively arranged in each of the peripheral zones 58, 58'. However, the number and the geometric shape of these recesses are not limited to the number and the circular shape shown.

In the embodiment shown, the ratio between the web width and the slot width or diameter amounts to 60%. The bottom illustration shows the measuring protocol with the horizontal temperature distribution along three broken lines 59', 59", 59'". The vertical temperature distribution can likewise be read out of the measuring protocols. The lines 59', 59", 59''' were chosen at a height, at which the tubes are subsequently severed in the inventive device.

The protocol is based on recordings with a thermal imaging camera. This protocol shows the horizontal temperature distribution along the lines 59', 59", 59'. The profile "line 3" corresponds to the measurement along the line 59'. The profile "line 1" corresponds to measurement along the line 59" and the profile "line 2" corresponds to measurement along the line 59'. The values of the pixels plotted on the y-axis correspond to horizontal length units along the lines 59', 59", 59'.

In order to measure the temperature distribution, the welding knife 56 was clamped into the welding knife holder 40, which comprises the first and the second clamping part 43, 44, and blackened for the measurement. The welding knife closes the secondary circuit of the transformer unit and is heated to a nominal temperature of about 300° C. due to its high resistance value. It was determined that the optimal temperature distribution (300° C.+/−5° C.) was reached within 3-4 seconds. Tests furthermore showed that the contacting of the welding knife by the two clamping parts affects the vertical temperature distribution. A symmetric distribution of the clamping force along the two peripheral zones proved relevant for the vertical temperature distribution. One option in this respect would be pressure pads that are preferably spring-molded on at least one of the two clamping parts. These pressure pads make it possible to achieve symmetric contacting by approximately adjusting the pressure of all pressure pads to the same value.

LIST OF REFERENCE SYMBOLS

1 Tubes of first group of tubes
1' Cut ends of tubes of first group of tubes
1" Residual ends of tubes of first group of tubes
2 Tubes of second group of tubes
2' Cut ends of tubes of second group of tubes
2" Residual ends of tubes of second group of tubes
100 First tube holder
101 First tube clamp of first tube holder
102 Second tube clamp of first tube holder
51 First spring
11 Through-openings through first tube clamp of second tube holder
12 Through-openings through second tube clamp of first tube holder
200 Second tube holder
201 First tube clamp of second tube holder
202 Second tube clamp of second tube holder
203, 203' Second springs
21 Through-openings through first tube clamp of second tube holder
22 Through-openings through second tube clamp of second tube holder
31 First squeezing zone
32 Second squeezing zone
4 Welding knife
4' Additional welding knife
4", 4' Peripheral zones
40 Welding knife holder
41 Pair of crank brackets
42 Slot
43 First clamping part
44 Second clamping part
45 Second crank bracket
47 Cone
48 Recesses
49 Melting surface
50 Blade
51 First springs
52 Tracer wheel of second crank
53 Pair of tracer wheels of first crank
55 Crescent-shaped rails
56 Welding knife
57 Circular recesses
58, 58' Peripheral zone
59', 59", 59'" Three broken lines
400 Platform for positioning welding knife holder
401 Drive unit for platform
402, 403, 407 Gearwheels
404 Motor
405 Connecting rod
406 Rod-shaped guide
411 Four first cranks
431, 441 Angled clamping arms
451 Second crank
500 Box with welding knives
520 Rod-shaped guide
600 Welding knife feed
60 Slide
61 Guide rails
601 Carriage
602 Drive unit for welding knife feed
603 Synchronous belt
700 Table
70 Hollow cone
71 Fourth springs
72 Latch
720 Stopping face
701 Four legs
702 Cutout
704 Drawer
705 Start button
10, 20 Clamping levers
800 Return motion mechanism
80 Third spring
81 Tie rod
82 Stop
90 Transformer unit
901 Screw
902 Temperature sensor
Contacting position (A)
Pickup position (B)
Release position (C)

What has been described above are preferred aspects of the present innovation. It is of course not possible to describe every conceivable combination of components or methodologies for purposes of describing the present innovation, but one of ordinary skill in the art will recognize that many further combinations and permutations of the present innovation are possible. Accordingly, the present innovation is intended to embrace all such alterations, combinations, modifications, and variations that fall within the spirit and scope of the appended claims.

We claim:

1. A device for welding thermoplastic tubes of a first and a second group of tubes (1, 2), comprising two tube holders (100, 200) that respectively comprise a first (101, 201) and a second tube clamp (102, 202), as well as a welding knife (4), wherein the tubes of the first group of tubes (1) can be inserted into the through-openings (11, 21) of the two first tube clamps (101, 201) such that they continuously extend between the two tube holders (100, 200) in a straight manner and are squeezed therein, wherein the tubes of the second group of tubes (2) can be inserted into the through-openings (12, 22) of the two second tube clamps (102, 202) such that they continuously extend between the two tube holders (100, 200) in a straight manner and are squeezed therein, wherein the welding knife (4) can be moved between the first and the second tube holder (100, 200) and is provided for severing the squeezed tubes of the first and the second group of tubes (1, 2) in one motion in order to thereby produce cut ends (1', 2') and residual ends (1", 2"), wherein one of the two tube holders (100, 200) can be displaced relative to the other tube holder (100, 200) in order to thereby align the cut ends (1', 2') of the tubes with one another, and wherein the two tube holders (100, 200) can be displaced toward one another and away from one another in a horizontal direction in order to thereby simultaneously weld the cut ends (1') of the tubes of the first group of tubes (1) to their respectively aligned cut ends (2') of the tubes of the second group of tubes (2) into respective continuous tubes, wherein the through-openings (11, 21) of the two first tube clamps (101, 201) are arranged on a first plane and the through-openings (12, 22) of the two second tube clamps (102, 202) are arranged on a second plane, wherein the first plane is arranged parallel to the second plane and spaced apart therefrom.

2. The device according to claim 1, where the two first tube clamps (101, 201) and the two second tube clamps (102, 202) comprise squeezing zones (31, 32), wherein these squeezing zones (31, 32) extend along the through-openings (11, 21, 12, 22) and squeeze the inserted tubes at an oblique angle in relation to the first and/or the second plane respectively.

3. The device according to claim 1, wherein the welding knife (4) can be clamped in a welding knife holder (40) and a drive unit (401) is provided for moving the welding knife holder (40) in a vertical direction in order to sever the tubes, wherein one of the two tube holders (100, 200) can be vertically displaced relative to the other tube holder (100, 200) in order to align the cut ends (1', 2') of the tubes.

4. The device according to claim 3, wherein the two tube holders (100, 200) furthermore can be horizontally moved toward one another or away from one another or both tube holders (100, 200) can be simultaneously moved in one direction due to the motion of the welding knife holder (40) in the vertical direction.

5. The device according to claim 4, wherein the device comprises a platform (400), which that can be moved in the vertical direction, and the welding knife holder (40) is arranged on this platform (400).

6. The device according to claim 3, wherein the welding knife holder (40) comprises two opposite clamping parts (43, 44), between which the welding knife (4) can be clamped, wherein one of the two clamping parts preferably is stationary and the other clamping part can be moved relative to the stationary clamping part.

7. The device according to claim 6, wherein a pair of first crank brackets (41) is provided on at least one of the two clamping parts (43, 44) and the pair of crank brackets (41) preferably comprises a total of four first cranks (411), wherein these cranks (411) are identical to one another and arranged mirror-symmetrical referred to a plane of the welding knife (4) when the welding knife (4) is clamped between the two clamping parts.

8. The device according to claim 7, wherein pairs of tracer wheels (53) are provided in order to trace the cranks (411) during the motion of the welding knife holder (40) in the vertical direction and to thereby move the two tube holders (100, 200) horizontally toward one another or away from one another or to simultaneously move both tube holders (100, 200) in one direction.

9. The device according to claim 8, wherein a second crank bracket (45) and an additional pair of tracer wheels (52) is provided, wherein the additional pair of tracer wheels (52) is provided for tracing the second crank bracket (45) during the motion of the welding knife holder (40) in the vertical direction in order to move one clamping part (43) relative to the second stationary clamping part (44) and to thereby vary the distance between the two clamping parts (43, 44).

10. The device according to claim 9, wherein the second crank bracket (45) is traced by the additional tracer wheel (52), wherein three different positions can be assumed, namely a first contacting position (A), in which the distance between the two clamping parts is chosen such that the welding knife (4) is clamped in position and at the same time electrically contacted, a second position (C), in which the distance between the two clamping parts (43, 44) is chosen such that the welding knife can be ejected, and a pickup position (B), in which the distance between the two clamping parts (43, 44) is chosen such that the welding knife can be inserted between the two clamping parts (43, 44).

11. The device according to claim 10, wherein pressure pads are arranged on at least one of the two clamping parts (43, 44) and contact the welding knife (4) in the contacting position (A), wherein these pressure pads are spring-mounted on at least one clamping part (43, 44).

12. The device according to claim 6, wherein the device furthermore comprises a transformer unit (90) with a primary winding and a secondary winding, wherein the secondary winding is formed by a single conductor only and this conductor is connected to one of the two clamping parts (43, 44), preferably to the stationary clamping part (44), and wherein the welding knife (4) closes the secondary circuit in the contacting position (A) and is thereby heated to the desired temperature.

13. The device according to claim 1, wherein the first and the second group of tubes (1, 2) respectively comprise the same number of individual tubes, preferably more than two tubes, particularly six tubes per group of tubes (1, 2).

14. A method for welding a plurality of tubes of a first and a second group of tubes (1, 2) by a device according to claim 1, wherein the tubes of the first and the second group of tubes are in a first step inserted parallel to and on top of one another into opposite first (100) and second tube holders (200), namely such that they continuously extend between said tube holders in a straight manner, and squeezed therein, and wherein a heatable welding knife (4) is inserted into a welding knife holder (4) and heated to a desired temperature, the heated welding knife (4) is moved between the first and the second tube holder (100, 200) such that the squeezed tubes are simultaneously severed into cut ends (1', 2') and residual ends (1", 2"), the cut ends (1', 2") of the tubes are molten by the heated welding knife (4), the cut ends (1') of the tubes of the first group of tubes (1) are aligned with the cut ends (2') of the tubes of the second group of tubes (2) by displacing one of the two tube holders (100, 200) relative to the other tube holder (100, 200) such that the cut ends (1') of the tubes of the first group of tubes (1) are arranged symmetrically opposite of the cut ends (2') of the second group of tubes (2), the two tube holders (100, 200) are displaced toward one another in order to thereby simultaneously weld the cut ends (1') of the tubes of the first group of tubes (1) to their respectively aligned cut ends (2') of the tubes of the second group of tubes (2) into respective continuous tubes and the welding knife (4) is ejected from the welding knife holder (40).

15. The method according to claim 14, wherein the horizontal distance between the first and the second tube holder (100, 200) amounts to d1 during the insertion of the welding knife (4), that this distance is increased to d4 when the squeezed tubes are severed, that the distance amounts to d2 when the cut ends are molten, wherein d1<d2<d4 applies, that the distance is once again increased to d4 during the displacement of one of the two tube holders (100, 200), that the distance amounts to d3 during the welding operation, wherein d3<d4 applies, and that the distance between the two tube holders (100, 200) amounts to d5 during the ejection of the welding knife from the cut ends (1', 2'), wherein d5 represents the shortest of all five distances (d1, d2, d3, d4).

\* \* \* \* \*